United States Patent
Moll et al.

(10) Patent No.: US 7,801,746 B2
(45) Date of Patent: Sep. 21, 2010

(54) DIALYSIS STATION

(75) Inventors: Stefan Moll, Melsungen (DE); Gerhard Bock, Friedewald (DE); Dirk Moeller, Altmorschen (DE); Sandor Dolgos, Szentendre (HU)

(73) Assignee: B. Braun Medizintechnologie GmbH, Melsungen (DE)

( * ) Notice: Subject to any disclaimer, the term of this patent is extended or adjusted under 35 U.S.C. 154(b) by 2036 days.

(21) Appl. No.: 10/797,354

(22) Filed: Mar. 10, 2004

(65) Prior Publication Data

US 2004/0220832 A1 Nov. 4, 2004

(30) Foreign Application Priority Data

Mar. 11, 2003 (DE) ................. 103 10 873

(51) Int. Cl.
*A61B 5/00* (2006.01)
*G06F 19/00* (2006.01)
(52) U.S. Cl. ............ 705/3; 705/2; 705/4; 600/513; 128/903; 128/904; 210/143
(58) Field of Classification Search .......... 705/2–4; 210/143; 600/513; 128/903, 904
See application file for complete search history.

(56) References Cited

U.S. PATENT DOCUMENTS

| 5,339,821 A * | 8/1994 | Fujimoto ............ 600/513 |
| 6,269,340 B1 * | 7/2001 | Ford et al. ............ 705/3 |
| 6,284,131 B1 * | 9/2001 | Hogard et al. ............ 210/143 |

FOREIGN PATENT DOCUMENTS

WO  WO 02/069793 A2  9/2002

* cited by examiner

*Primary Examiner*—Gerald J. O'Connor
*Assistant Examiner*—Linh Michelle Le
(74) *Attorney, Agent, or Firm*—RatnerPrestia

(57) ABSTRACT

A dialysis station including several patient places each of which is provided with a dialyzer and a video terminal. In an internal data network, the video terminals are interlinked with each other and with a server including a data base. At a physician place, the treatment course can be followed for each patient place. If necessary, the physician may intervene and prescribe a new or changed medication appearing on the video terminal of the patient place. After having administered the medicine, the nurse acknowledges the administration of the medicine. The dialogue taking place between physician and nurse is documented in the scope of the treatment course.

20 Claims, 6 Drawing Sheets

MASTER DATA

STANDARDMAN, Martin (01.01.1940), 14.01.2003 09:52:20

PATIENT | SESSION | RISKS

- PERSONAL IN CHARGE
- GROUP
- STATION
- ROOM
- BED/PLACE

PRESENT CARD STACKER PLACE

START OF SESSION: 14.01.2003 09:52:20
END OF SESSION:

☐ SESSION EXAMINED AND ACCEPTED BY PHYSICIAN

[TRANSFER SESSION DATA TO EXTERNAL DATA BASE NOW]

[CLOSE THIS SESSION NOW]

[OK] [ABORT] [ACCEPT] [CANCEL]

Fig. 2

CHECKLIST

STANDARTDMAN, Martin (01.01.1940), 14.01.2003 09:52:20

| Index | Status | ENTRY |
|-------|--------|-------|
| 1 | ☐ | STORAGE |
| 2 | ☐ | PERFORM NUTRITIONAL CONSULTING ACCORDING TO PLAN |
| 3 | ☑ | ADMINISTER MEDICINES |
| 4 | ☐ | NOTIFY TRANSPORT IN TIME |

[OK] [ABORT] [ACCEPT] [CANCEL]

Fig. 3

DIALYSIS STATION

BACKGROUND OF THE INVENTION

1. Field of the Invention

The invention relates to a dialysis station with at least one patient place and a central server.

2. Description of Related Art

A station with several patient places for the extracorporeal blood treatment is disclosed in International Patent WO 02/069793 A2. This blood treatment system comprises several blood treatment apparatus each of which is provided with a video terminal. Each of the video terminals, configured as touch screens, forms an input/output unit by which the operating personnel is able to input data into the respective blood treatment apparatus. In such cases, no central server is necessary which would be necessary otherwise. The operator may also input information on possible occurrences or the condition of the patient at the video terminal. The video terminals are linked among each other and with the server to form an internal network. Other video terminals which are not allocated to a special patient place may also be connected to this internal network. These decentralized stations form independent communication units. The server includes a patient management system in which patient data and the treatment history are stored.

SUMMARY OF THE INVENTION

It an the object of the present invention to provide a dialysis station comprising a central server and at least one patient place, where it is not only possible to monitor the treatment at each patient place from a physician place but also to intervene into this treatment, and where a dialogue between the physician place and the patient place is possible via the data network.

This object is achieved by providing a dialysis station according to the invention. Specifically, the dialysis station according to the invention comprises at least one patient place having a dialyzer and a video terminal allocated thereto, a central server including a data base with a patient data file and an operational data and status data file of the individual dialyzers, and a physician place equipped with at least one video terminal, the video terminals and the server being interlinked with each other and configured such that information on the treatment course at a selected patient place can be called at the physician place and that instructions and operational parameters for a selected patient place are adapted to be input at the physician place. An acknowledgment of the execution of an instruction is made in that the executing person acknowledges his or her identity.

According to the invention, the acknowledgment of the identity is an acknowledgment of the execution of an instruction at the same time and is preferably stored. In a way, this acknowledgment has the function of a signature.

The dialysis station according to the invention permits identification of the person making adjustments at the patient place, these adjustments being able to be made on the basis of an instruction of the physician at a remote place. Thus, there is an additional check that a certain instruction has been executed at a patient at the correct patient place—and thus at the intended patient. In the case of an instruction, this instruction is executed first and, subsequently, the executing person is identified on the basis of a password, a chip card, a magnetic card, and the like. The accepted acknowledgment of the identification simultaneously goes along with the report on the execution of the instruction to the physician place.

In dialysis, there is an increasing obligation to keep a record of all measures performed. A group of nursing personnel is always in charge of a certain group of patients. Therefore, it is important that instructions are executed at precisely that patient place for which they are intended. The invention permits an acknowledgment of the definite allocation of an instruction to a patient place. The acknowledgment of the identity of the executing person can be effected in that the person presses an "OK" key after he or she has input a password or an ID number. It may also be effected by reading in a data carrier carrying an ID identification into the machine. In this case, no OK key is required.

The dialysis station according to the invention permits a bidirectional data communication between the physician place and each patient place. It is possible to directly intervene into the operation of each respective dialyzer from the video terminal of the physician place, and the operational parameters of the dialyzer can be changed by the physician. The operational parameters can be displayed and changed at the video terminal of the patient place as well, the change, if necessary, requiring a special authorization of the respective person and being registered in the system.

All patient-related data and all machine-related data of a patient place which can be displayed at the video terminal of the physician place can also be displayed at the video terminal of the respective patient place. The video terminal of the physician place can be switched to any of the patient places. The video terminal of a patient place, however, only shows the data of the dialyzer of this patient place and the respective patient. Only these data can be changed at the patient place.

The operational parameters set for a patient are either data pre-stored in the server or data read out from a chip card of the patient or data calculated from certain measured values, e.g., the weight of the patient, or data carried over from the last treatment. Inputting operational parameters requires the subsequent input of an ID identification of the executing person. The identity of the inputting person as well as the time of input are stored in the computer together with the respective instruction. It may also be provided that the instruction given by the physician has to be provided with an ID identification of the physician and acknowledged before this instruction is transferred to the patient place. In this case, the instruction of the physician is stored along with the ID identification.

The central server includes a patient data file with the master data of the patient and information on particular sensitivities or tolerances as well as the operational and status data file of the individual dialyzers. Thus, it can be detected, for example, that a particular patient is only allowed to be treated at a certain type of dialyzer. The operational and status data file of the dialyzers also receives the operational parameters to be set for a patient.

The invention permits a physician to supervise a selected dialysis from the physician place and actively intervene into this dialysis. The intervention may be effected in that machine parameters are changed or that a particular medication is prescribed that has to be manually administered by the nurse at the patient place. The prescription of the medication as well as the reply or acknowledgment of the execution of the respective instruction is effected via the data network. Subsequently, the dose of the medication is stored in the server along with the point in time. The server contains the history of each individual dialysis. Therefore, it also forms a documentation device.

The video terminals of the patient places, of the physician place, and the server may be connected with each other to form an internal network, e.g., by a bus data system. The internal network, however, may also be connected to an external network. Thus, a physician place from the external network is able to communicate with each patient place. Thus, the physical presence of the physician in the dialysis station is not required.

By the term "video terminal," an input/output station is to be understood which has a display and is prepared for the processing of data. Preferably, it is a PC. The video terminal may also comprise a touch screen at which instructions and data can be input by touching certain fields. In this case, it can be done without a keyboard or a mouse.

At the patient place, an ID input device is provided for the identification of patients and/or personnel. Such an input device is, e.g., a chip-reading apparatus into which the chip card of a patient is input. The chip card includes certain patient data and patient information. These are transferred to the server which then transmits the related information from the patient data file to the video terminal of the patient place. Thus, a distinctive allocation of the patient to the respective dialyzer is effected.

It is also possible to allocate an identification code to each operating person, which has to be input into a keyboard.

BRIEF DESCRIPTION OF THE DRAWINGS

Hereinafter, embodiments of the invention will be explained in detail with reference to the drawings, in which:

FIG. 2 is a screen surface for inputting patient data, FIG. 3 is a screen surface with a checklist for a selected patient.

DETAILED DESCRIPTION OF THE INVENTION

Figure 1:
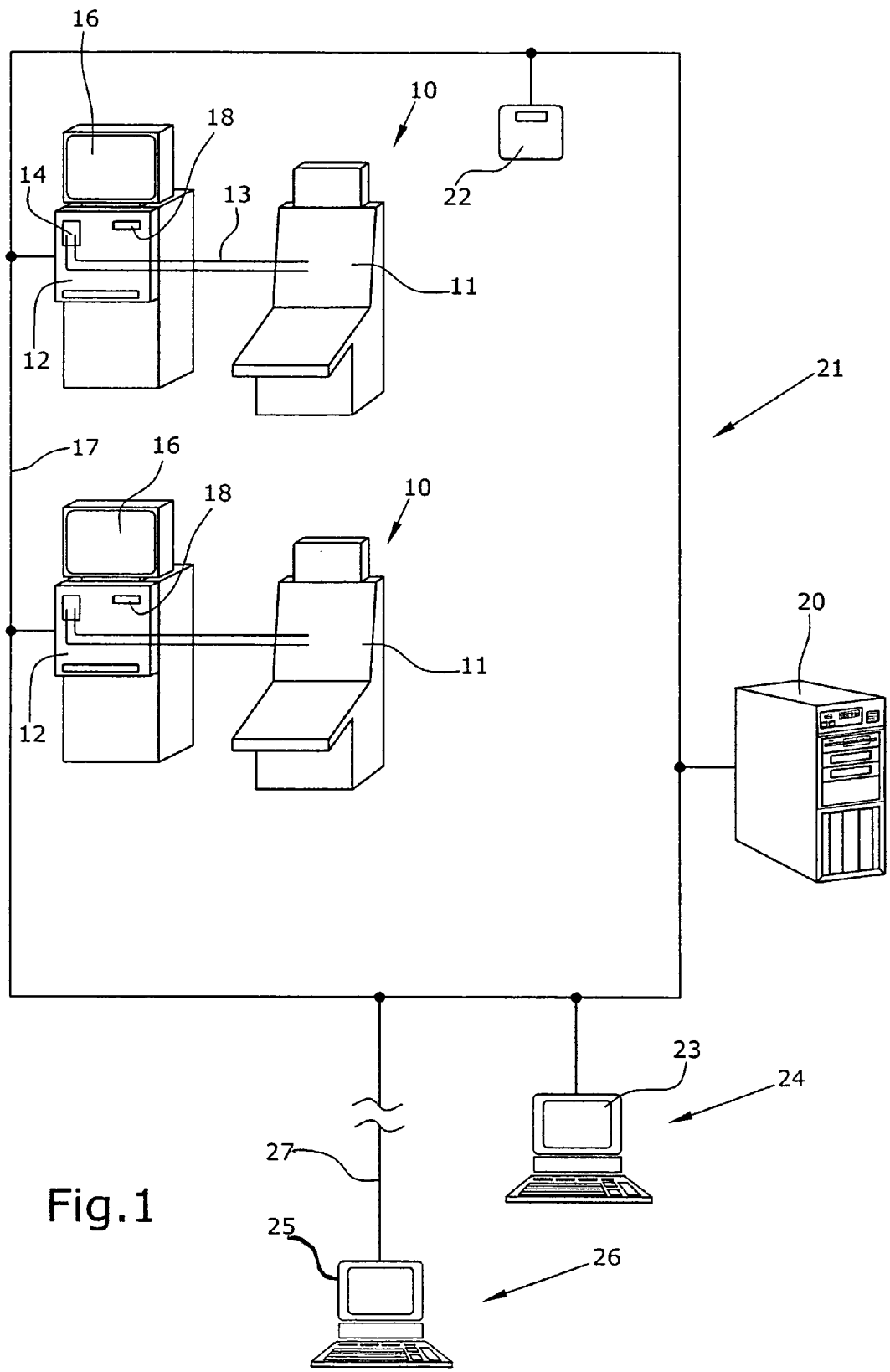
FIG. 1 is a schematic block diagram of the dialysis station according to the present invention.

In FIG. 1, a dialysis station with several patient places 10 is illustrated. Each patient place 10 is provided with a corresponding bed or chair 11 as well as with a dialyzer 12. The dialyzer 12 is a dialysis machine connected with the patient's body via a hose system 13 and including, inter alia, a blood pump 14.

The dialyzer 12 is provided with a video terminal 16 comprising a touch screen forming an input/output device for a (non-illustrated) PC operatively connected with the controlling and measuring system of the dialyzer. The dialyzers 12 and the video terminals 16, respectively, are connected with each other and with a central server 20 via a data bus line 17 in order to form an internal network 21. Further, electronic scales 22 for weighing the patient as well as a video terminal 23 arranged at a central physician place 24 are connected with the network 21. A further video terminal 25 may be arranged at an external physician place 26 connected with the internal network 21 by an external network 27. Thus, there is an additional access to the internal network 21 from a remote location.

The server 20 contains a data base and performs the entire management of all machine and patient data.

The dialyzer 12 has a reading apparatus 18. It is a chip card reader for reading out data from a chip mounted on a chip card. The chip card serves to identify the operating person and the patient. By reading the chip card, the operating person and the patient are distinctly allocated to the respective dialyzer.

Such a reading apparatus 18 is included in all the apparatus provided for the treatment of the patients, e.g., the scales 22 or laboratory apparatus as well.

The documentation and storage of patient data not measured by the dialyzer 12 is not effected on paper but exclusively in one of the connected computers, i.e., either in the computer of the patient place 10 or the physician place 24,26. Such patient data include the medication, indications on the well-being, and laboratory values. The documentation of patient data during the treatment is always effected at the patient place 10. The patient information is put to the disposal of the server 20 and the respective physician place 24,26. Instructions to the operating personnel are sent from the physician place 24,26 to the patient place 10. The respective video terminal draws the attention of the patient or the personnel to the arrival of a respective instruction by an alarm. Following the instruction has to be acknowledged by the personnel.

FIG. 2 shows a session mask as screen surface. In the field 30, the name and date of birth of the patient as well as the date of session and the present time are listed. Below, different information on the session have to be entered into respective fields 31.

FIG. 3 shows a checklist in the form of a screen surface. Under the category "Entry," the checklist includes a number of activities that have to be carried out by the personnel in connection with a session. The execution of the activity is acknowledged by checking off under the category "Status."

Figures 4, 5:
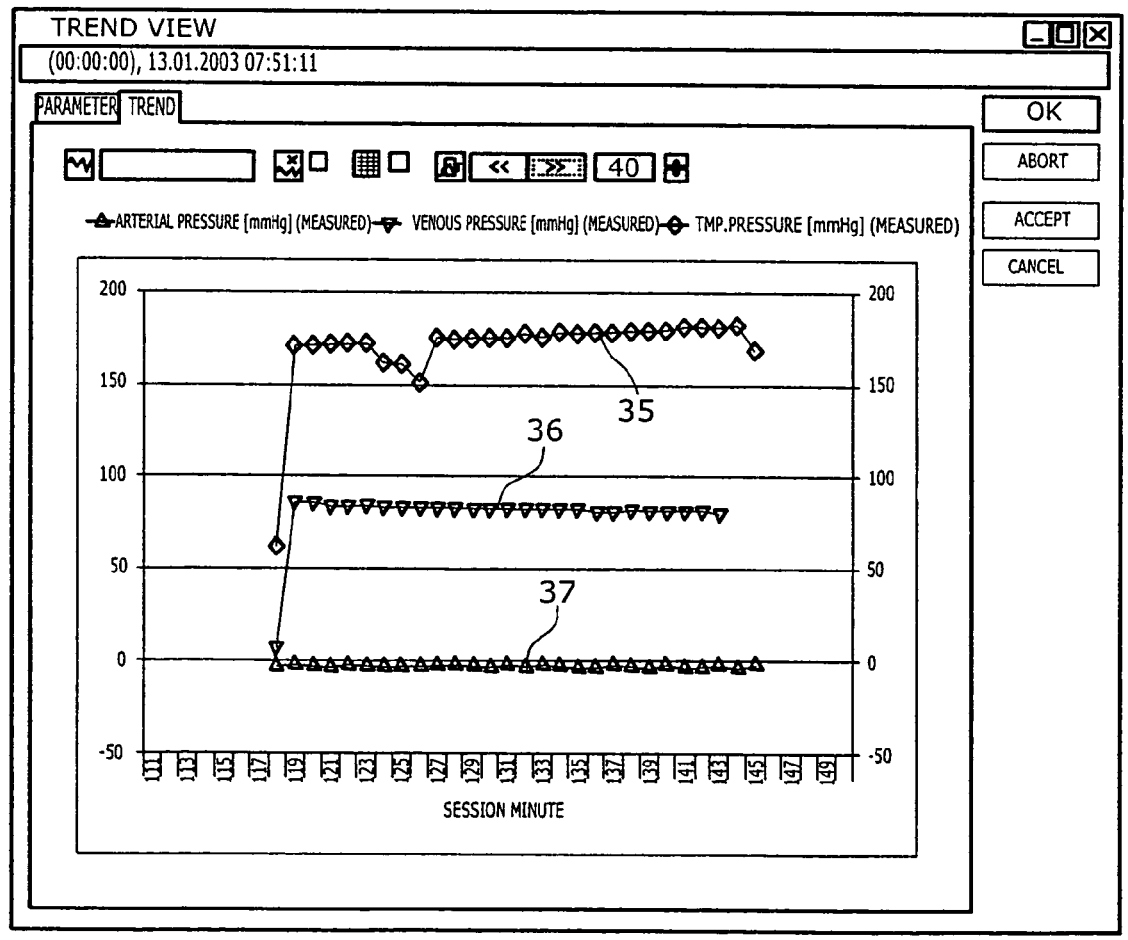
FIG. 4 is a screen surface where the medication of the respective patient is indicated.
FIG. 5 is a screen surface with curves of the arterial blood pressure, the venous blood pressure, and the trans-membrane pressure over the course of time.

FIG. 4 shows a screen surface with the title "Medication." The medicines to be administered to the patient are listed therein. Under the category "Date/Time" the intended time appears before the medicine will be administered; and after it has been administered, the execution time appears.

Generally, the medication instruction is prescribed by the physician. The physician may enter it at the physician places 24 and 26, respectively. As a basis for the medication, the physician has patient-specific parameters at his disposal, like those illustrated in the trend view of FIG. 5, for example.

In FIG. 5, the upper curve 35 indicates the course of the transmembrane pressure TMP of the dialyzer over time, the central curve 36 the course of the venous blood pressure over time, and the lower curve 37 the course of the arterial blood pressure over time during a session of a patient. These values are detected at specified intervals and stored in the server 20. The physician is able to specifically call the respective curves and other information onto his video terminal to set the medication accordingly.

Figure 6:
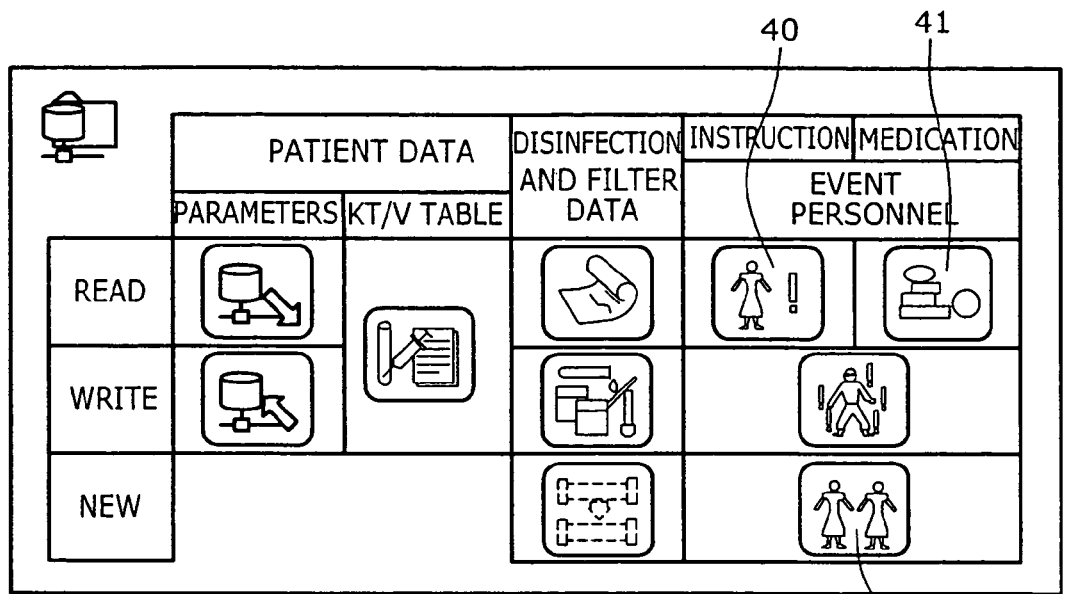
FIG. 6 shows a screen surface for the communication between physician and operating personnel.

FIG. 6 shows a screen mask with different symbols (icons) for the video terminal 16 of the patient place 10. Symbol 40 means the existence of a treatment instruction, i.e., an instruction to the personnel to execute certain instructions. The symbols are configured as switching surfaces of a touch screen. Symbol 41 indicates the existence of a medication instruction. If this switching surface is touched, the medication instruction appears. Symbol 42 means a request to the personnel to make an identification, i.e., to enter an ID number or the name.

Figure 7:
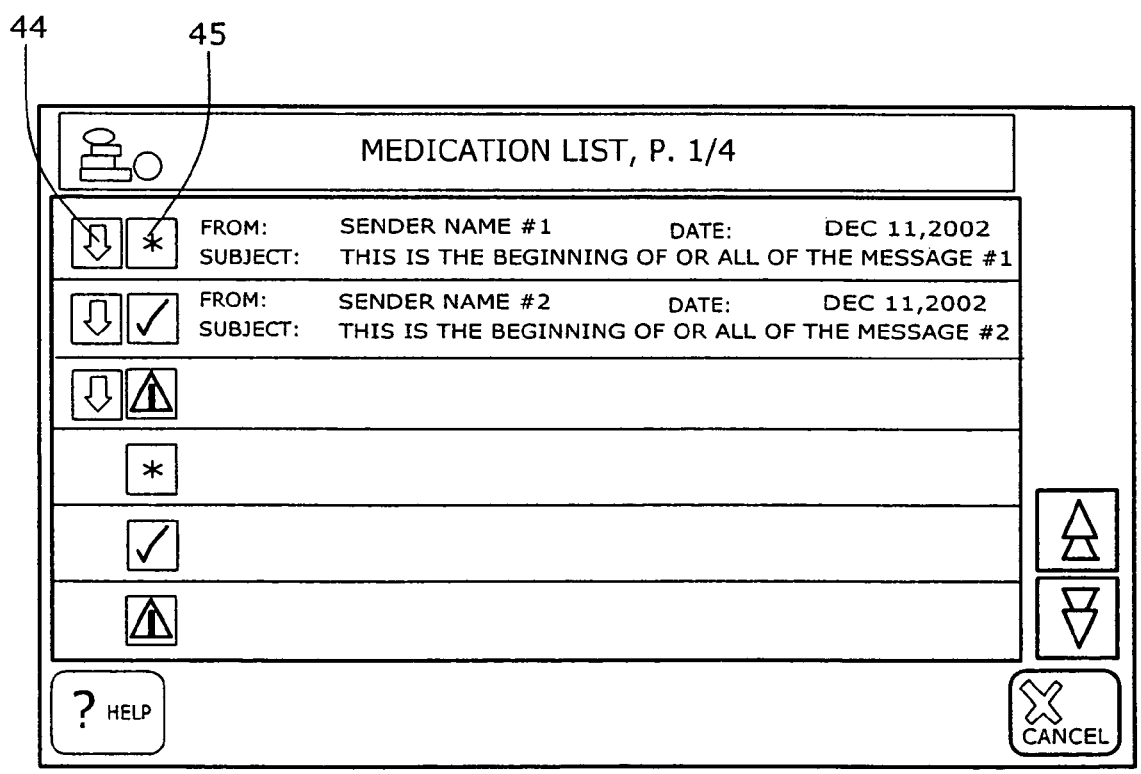
FIG. 7 shows a screen surface with a medication list.

FIG. 7 shows the medication instruction appearing in FIG. 6 after the symbol 41 has been touched. Upon touching, the arrow symbols 44 respectively open the complete text. The symbols in column 45 indicate the state of the medication, e.g.: due (asterisk), executed (check), and not due yet (exclamation mark in triangle). The medication list is prescribed and changed from the physician place 24,26. At the patient place 10, it can only be changed after a corresponding identification of the physician. The name of the physician making an entry is also taken up into the medication list.

Figure 8:
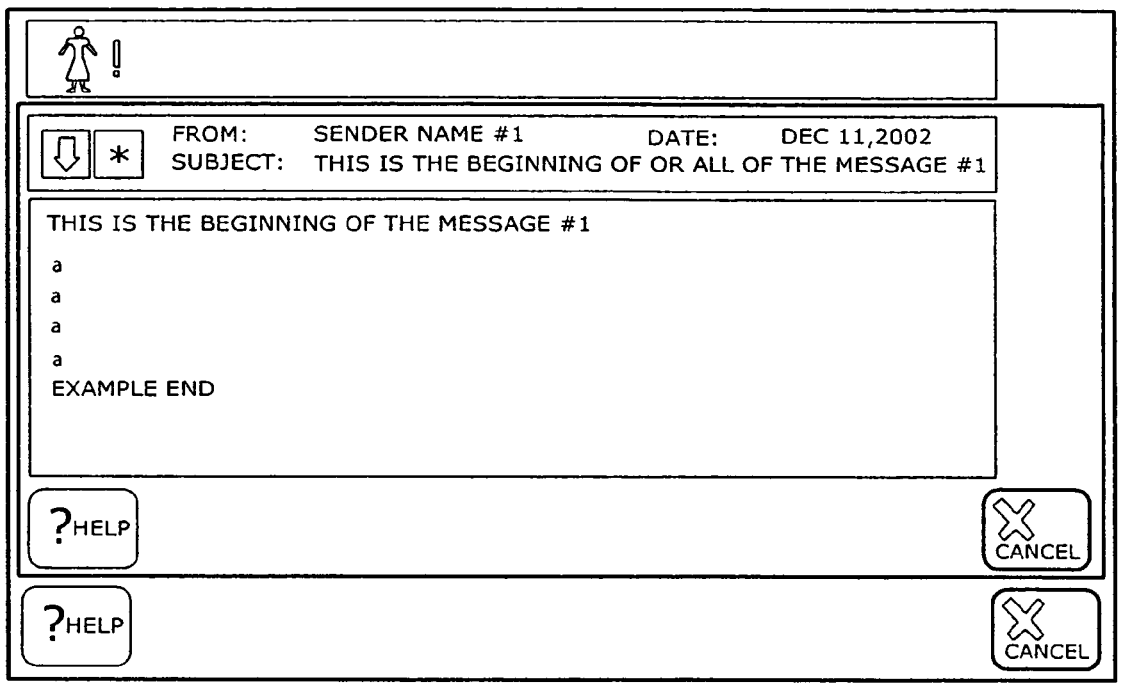
FIG. 8 shows a screen surface with an instruction list.

In FIG. 8, the instruction list (list of treatment instructions) is illustrated which appears after touching the symbol 40 in FIG. 6. This list, e.g., includes the times at which a certain treatment at the patient has to be performed, e.g., "measuring the body temperature." After an instruction of the list has been executed, this is acknowledged by the operating person by pressing an acknowledgment key 50 provided at the apparatus as a hardware key.

Figure 9:
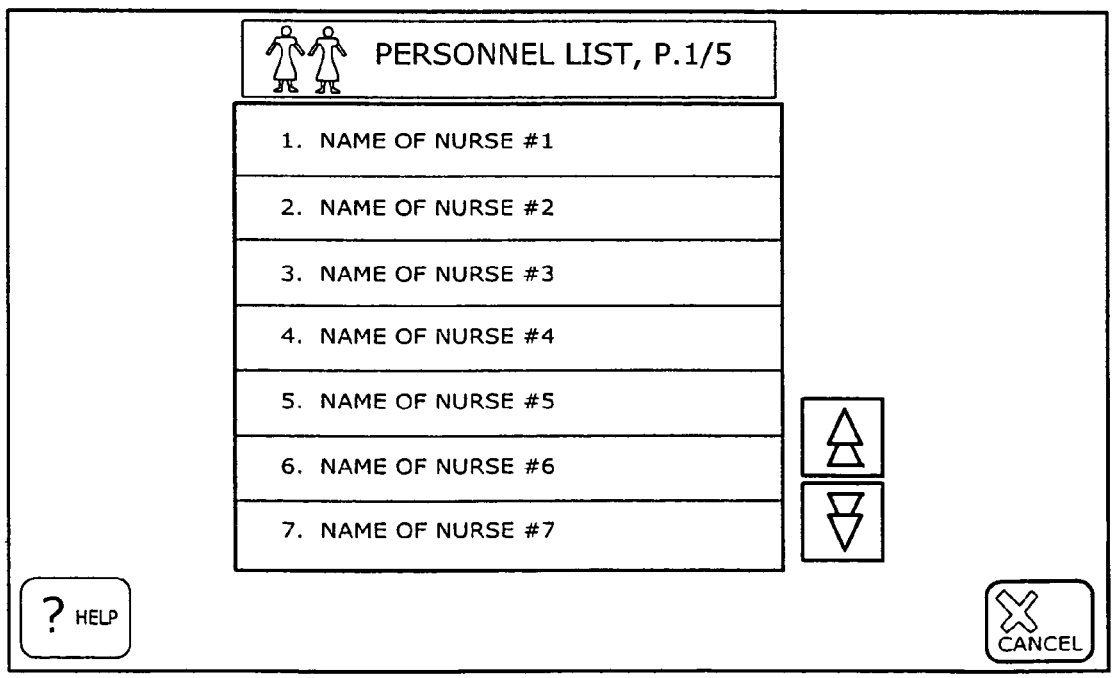
FIG. 9 shows a screen surface with a personnel list.
Figure 10:
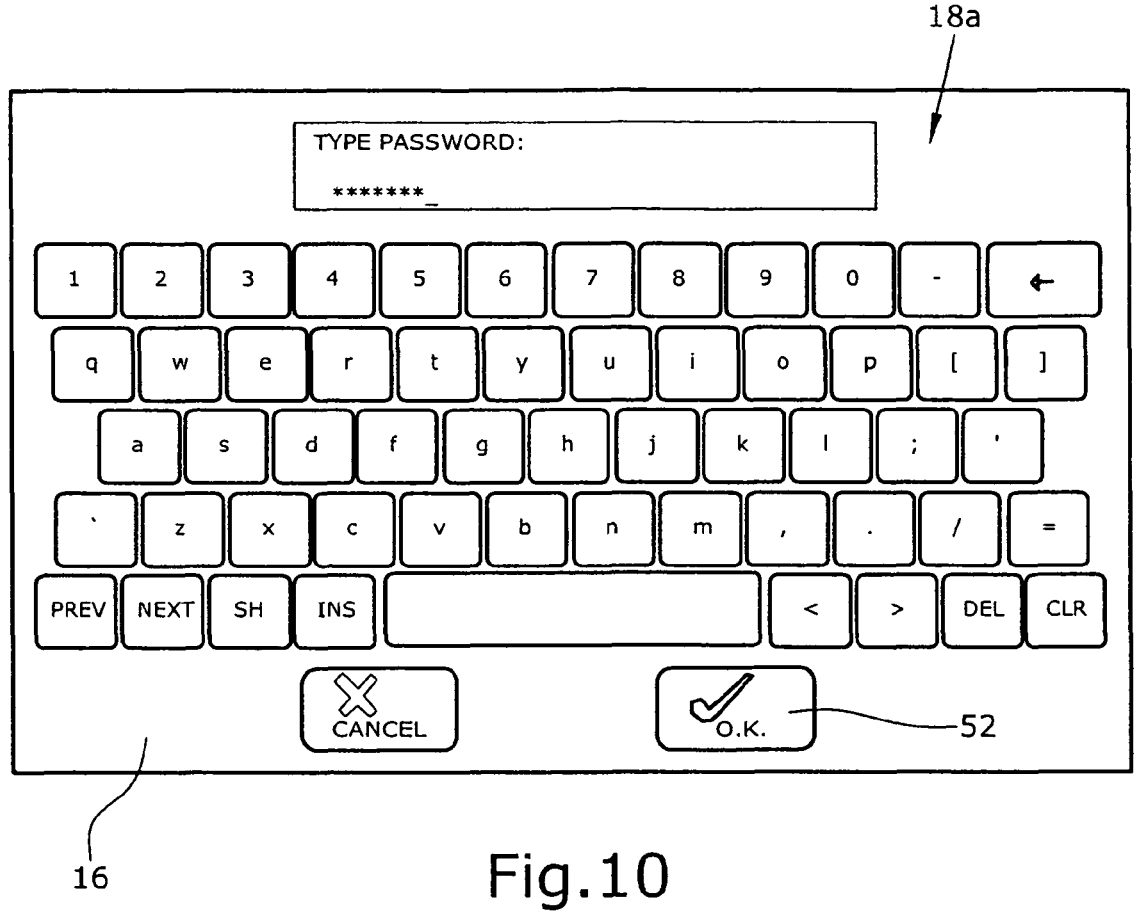
FIG. 10 shows a screen surface for the password input.

FIGS. 9 and 10 show the screen surface for the subsequent password entry of the personnel. First, the personnel list with the names of the respective nurses appears. The respective nurse may select and touch her name and acknowledge it by pressing the OK key 50. Thereafter, the alphanumeric keyboard illustrated in FIG. 10 appears. The nurse can input her ID number or a password. This is acknowledged by the OK key 52. Thereupon, the nurse is identified. Pressing the OK key 52 is the acknowledgment of the execution of the instruction at the place of work. With this variant, the screen mask illustrated in FIG. 10 forms the ID input device 18a for identifying the personnel.

Hereinafter, an example of a treatment course is indicated:

1. The patient enters into the dialysis center and identifies himself with an identification card at the scales 22. The patient weight is compared with the nominal weight and the difference is stored as nominal ultrafiltration for the following treatment.

2. The patient goes to any patient place 10 at all and identifies himself with his card there again. The apparatus automatically begins to prepare itself. From the data base of the server 20, the dialyzer settings and data desired for this patient are loaded, e.g., UF quantity, UF rate, blood pump speed, dialysate conductivity, and the like. These data have either been calculated (from the weighed weight), input by the physician or another authorized person, or carried over from the last treatment.

3. The patient is connected; the apparatus data transferred are used for the dialysis.

4a. The nurse in charge also identifies herself at the dialyzer.

4b. During the dialysis, problems occur that require the apparatus parameters to be changed. The apparatus parameters are input. Together with the code of the person who has made the change, the new data are stored in the data base.

5. Actions at the patient and information on the patient's condition are also documented at the machine and stored in the data base after they have been provided with a time stamp. (Example: the patient is sick and is administered 5 ml of medicine X.) Thus, all data of the treatment of the special patient are available in the system and describe the quality of the treatment. Confusing the patient and treatment data is impossible once the patient has been identified.

6. The physician at the physician place 24 contemporarily sees the correlations between machine data, medication, and patient condition. He reacts with an instruction (e.g., another 5 ml of medicine X). This instruction directly appears at the machine at which the respective patient is located.

7. The instruction of the physician is obeyed, and the completion is again acknowledged by the nurse by inputting her ID code. The physician directly receives a reply as to the execution. The data are stored and can be processed further (e.g., repeat order of 10 ml of medicine X).

The personnel sees the respective instructions at the dialyzer. After the instruction has been executed and the acknowledgment has been performed at the video terminal, it transmits the acknowledgment to the server 20 on which the success of the job instruction is stored and can be shown for subsequent examinations. Moreover, the personnel is able to input measures performed without job instruction at the video terminal 16, which are also transmitted to the server 20 either with or without identification. Furthermore, it is possible to input occurrences appearing during the treatment, e.g., a drop of blood pressure, which are then transmitted to the central computer.

It is advantageous that only the data for the treatment of the respective patient appear on the video terminal 16 of the patient place 10, that the personnel is able to input the protocol and remarks relating thereto directly at the dialyzer 12, that the attention of the personnel is drawn to instructions of the physician directly at the screen, and that the executions thereof are supervised.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

The invention claimed is:

1. A dialysis system for implementing a course of treatment for a patient as instructed by a medical personnel and executed by a person, the dialysis system comprising:
    at least one patient place having a dialyzer, a video terminal, and an ID input device for inputting an identification;
    a central server including a data base; and
    at least one physician place equipped with a video terminal, said video terminals of the at least one patient place and the at least one physician place and the server being interlinked with each other and configured such that information on the course of the treatment at a selected patient place is callable and instructions for a selected patient place are adapted to be input;
    wherein the system is configured such that information on the execution of an instruction can be input at the patient place and the execution of an instruction is acknowledged by the executing person acknowledging his or her identity at the ID input device.

2. The dialysis system according to claim 1, wherein information on occurrences can be input at the patient place, and an acknowledgment of the input is effected in that the executing person acknowledges his or her identity in the ID input device.

3. The dialysis system according to claim 1, wherein a patient code can be input which allocates the patient place to a patient.

4. The dialysis system according to claim 1, wherein the video terminal of the patient place is configured as a user interface for setting and changing parameters of the dialyzer, and the setting and change are stored along with the identity of the executing person.

5. The dialysis system according to claim 1, wherein the video terminals of the at least one patient place and the physician place are connected in an internal communication network.

6. The dialysis system according to claim 5, wherein the internal communication network is connected with an external communication network to which a video terminal of an external physician place is connected.

7. The dialysis system according to claim 1, wherein a symbol for calling an instruction input at the physician place can be illustrated on the video terminal of the at least one patient place.

8. The dialysis system according to claim 1, wherein a patient data file stored in the server includes indications on the dialyzer determined for a patient as well as on the settings and operational parameters thereof, and the video terminal of the at least one patient place receives the settings and operational parameters from the server and sets them at the dialyzer.

9. The dialysis system according to claim 1, wherein the input device consists of a data reader reading information on the patient, the operator, or both from a data carrier.

10. The dialysis system according to claim 1, wherein each video terminal comprises a screen with a keyboard and a computer connected with a control portion of the dialyzer.

11. A dialysis system for implementing a course of treatment for a patient as instructed by a medical personnel and executed by a person, the dialysis station-system comprising:
　　at least one patient place having a dialyzer, a video terminal, and an ID input device for inputting an identification;
　　a central server including a data base; and
　　at least one physician place equipped with a video terminal,
　　the video terminals and the server being interlinked with each other and configured such that information on the course of the treatment at a selected patient place is callable and instructions for a selected patient place are adapted to be input,
　　wherein the system is configured such that information on the execution of an instruction can be input at the patient place and the execution of an instruction is acknowledged by the executing person acknowledging his or her identity at the ID input device, and wherein a patient code can be input which allocates the at least one patient place to a patient, the video terminal of the at least one patient place is configured as a user interface for setting and changing parameters of the dialyzer, and the setting and change are stored along with the identity of the executing person.

12. The dialysis system according to claim 11, wherein the video terminals of the at least one patient place and the physician place are connected in an internal communication network, the internal communication network connected with an external communication network to which a video terminal of an external physician place is connected.

13. The dialysis system according to claim 11, wherein a symbol for calling an instruction input at the physician place can be illustrated on the video terminal of the at least one patient place.

14. The dialysis system according to claim 11, wherein a patient data file stored in the server includes indications on the dialyzer determined for a patient as well as on the settings and operational parameters thereof, and the video terminal of the at least one patient place receives the settings and operational parameters from the server and sets them at the dialyzer.

15. The dialysis system according to claim 11, wherein the input device consists of a data reader reading information on the patient, the operator, or both from a data carrier.

16. The dialysis system according to claim 11, wherein each video terminal comprises a screen with a keyboard and a computer connected with a control portion of the dialyzer.

17. A dialysis system for implementing a course of treatment for a patient as instructed by a medical personnel and executed by a person, the dialysis system comprising:
　　at least one patient place having a dialyzer, a video terminal, and an ID input device for acknowledging an identification;
　　a central server having a data base and a patient data file stored in the server, the patient data file including indications on the dialyzer determined for a patient as well as on the settings and operational parameters thereof, and the video terminal of the at least one patient place receives the settings and operational parameters from the server and sets them at the dialyzer; and
　　at least one physician place equipped with a video terminal, wherein the video terminals of the at least one patient place and the physician place are connected in an internal communication network, the internal communication network connected with an external communication network to which a video terminal of an external physician place is connected,
　　the video terminals and the server being interlinked with each other and configured such that information on the course of the treatment at a selected patient place is callable and instructions for a selected patient place are adapted to be input,
　　wherein the system is configured such that: information on the execution of an instruction can be input at the patient place and the execution of an instruction is acknowledged by the executing person acknowledging his or her identity at the ID input device; information on occurrences may be input at the patient place and such input is effected in that the executing person acknowledges his or her identity in the ID input device; and a patient code can be input which allocates the at least one patient place to a patient, the video terminal of the at least one patient place is configured as a user interface for setting and changing parameters of the dialyzer, and the setting and change are stored along with the identity of the executing person.

18. The dialysis system according to claim 17, wherein a symbol for calling an instruction input at the physician place can be illustrated on the video terminal of the at least one patient place.

19. The dialysis system according to claim 17, wherein the input device consists of a data reader reading information on the patient, the operator, or both from a data carrier.

20. The dialysis system according to claim 17, wherein each video terminal comprises a screen with a keyboard and a computer connected with a control portion of the dialyzer.

* * * * *